United States Patent [19]

McAleer et al.

[11] 4,181,713

[45] Jan. 1, 1980

[54] ISOLATION OF HB$_S$AG

[75] Inventors: William J. McAleer, Ambler; Edward H. Wasmuth, Telford, both of Pa.

[73] Assignee: Merck & Co., Inc., Rahway, N.J.

[21] Appl. No.: 955,863

[22] Filed: Oct. 30, 1978

[51] Int. Cl.$^2$ .................. A61K 39/00; A61K 39/12; A61K 39/42

[52] U.S. Cl. .................. 424/86; 260/112 B; 260/112 R; 195/1.4; 424/89

[58] Field of Search .................. 424/86, 89; 195/1.4; 260/112 B, 112 R

[56] References Cited

U.S. PATENT DOCUMENTS

| | | | |
|---|---|---|---|
| 3,951,977 | 4/1976 | Vnek et al. | 260/112 B |
| 3,976,767 | 8/1976 | Neurath | 424/89 |
| 3,994,870 | 11/1976 | Neurath et al. | 260/112 R |
| 4,017,360 | 4/1977 | Bertland et al. | 195/1.4 |
| 4,024,243 | 5/1977 | McAleer et al. | 424/89 |
| 4,087,519 | 5/1978 | Trepo | 424/86 |
| 4,088,748 | 5/1978 | McAleer et al. | 424/89 |
| 4,113,712 | 9/1978 | Funakoshi | 260/112 R |
| 4,118,478 | 10/1978 | Prince et al. | 424/89 |
| 4,118,479 | 10/1978 | Prince et al. | 424/89 |
| 4,138,287 | 2/1979 | Andersson et al. | 195/1.5 |

OTHER PUBLICATIONS

Houwen et al., J. Immunol. Methods, 8(1-2):185-194(1975), "Isolation of Hepatitis B Surface Antigen by Affinity Chromatography on Antibody-Coated Immuno Adsorbents".

Burlev et al., ZH. Mikrobiol. Epidemiol. Immunobiol. 9:59-65, 1977 (recd. 1978), "Antigenic Determinants of Serum Proteins Revealed in the Structure of the Hepatitis B Surface Antigen by Affinity Chromatography".

*Primary Examiner*—Shep K. Rose
*Attorney, Agent, or Firm*—Donald J. Perrella; Julian S. Levitt

[57] ABSTRACT

High purity HB$_S$Ag is injected into guinea pigs to stimulate formulation of HB$_S$Ab-positive serum. Gamma globulins containing HB$_S$Ab are separated from the serum and the globulin fraction containing HB$_S$Ab is isolated and coupled to a Sepharose gel. HB$_S$Ag from HB$_S$Ag-positive plasma is adsorbed on the gel by formation of an HB$_S$Ab-HB$_S$Ag complex. HB$_S$Ag is eluted from the column and dialysed.

2 Claims, No Drawings

ISOLATION OF HB$_s$AG

BACKGROUND OF THE INVENTION

The present invention is directed to a process for the isolation of HB$_s$Ag and, more particularly, to a process for the isolation of HB$_s$Ag which includes the stimulation of antibody formation by injecting purified HB$_s$Ag into an appropriate mammalian host and isolating HB$_s$Ag from converted plasma by fixed bed immunoadsorption.

OBJECTS OF THE INVENTION

It is an object of the present invention to provide an improved method for isolating and purifying HB$_s$Ag. Another object is to provide a method for isolating and purifying HB$_s$Ag wherein high titer HB$_s$Ab is used to isolate HB$_s$Ag by fixed bed immunoadsorption. These and other objects of the present invention will be apparent from the following description.

SUMMARY OF THE INVENTION

High purity HB$_s$Ag is injected into guinea pigs to stimulate formation of HB$_s$Ab-positive serum. Gamma globulins containing HB$_s$Ab are separated from the serum and the globulin fraction containing HB$_s$Ab is isolated and coupled to a Sepharose gel. HB$_s$Ag from HB$_s$Ag-positive plasma is adsorbed on the gel by formation of an HB$_s$Ag-HB$_s$Ab complex. HB$_s$Ag is eluted from the column and dialysed.

DETAILED DESCRIPTION

According to the present invention highly purified HB$_s$Ag antigen is injected into a susceptible animal species. By a susceptible animal species is meant one which forms HB$_s$Ab in response to injection of HB$_s$Ag, e.g., guinea pigs, grivet monkeys and chimpanzees. The antigen may be present in a composition containing a physiologically acceptable medium, e.g. saline. An adjuvant, e.g. Freund's complete adjuvant, Adjuvant 65 (described in U.S. Pat. No. 3,149,036) or Adjuvant 65-4 (described in U.S. Pat. No. 3,983,228 and U.S. Pat. No. 4,069,313), or alum may also be present. The animal is bled at from 12 to 16 weeks post inoculation to obtain HB$_s$Ab-positive serum.

By highly purified HB$_s$Ag is meant a spherical particle substantially equivalent to that described in U.S. Pat. No. 4,017,360 having about the following properties:

| | |
|---|---|
| E$_{1\%}$ | 52.3 |
| OD$_{250\ nm}$ | 0.115 |
| OD$_{260\ nm}$ | 0.082 |
| Lowry protein (µg/ml) | 22.0 |
| CF units/ml | 128 |
| RIA units/ml | 8,000 |
| RIA units per µg protein | 364 |
| Particle diameter | 18–22 nm |

The serum is treated to separate a globulin fraction containing HB$_s$Ab, e.g. by dialysis against ammonium sulfate to precipitate gamma globulins containing HB$_s$Ab. Preferably the ammonium sulfate is from about 2 M to about 4 M. The dialysis is preferably carried out at lowered temperatures of from about 10° down to above about the freezing point of the solution. The ammonium sulfate is removed by a further dialysis treatment employing, e.g., phosphate buffered saline (PBS).

The dialyzed gamma globulins are then treated to isolate the 7 S globulin fraction containing purified HB$_2$Ab. This treatment is effected conveniently by means of chromatographic separation, e.g. by means of a cross-linked dextran such as Sephadex G-200, or a cellulose, such as DEAE-cellulose.

The isolated 7 S globulin fraction which is recovered as eluate from the chromatographic separation is coupled to activated CNBr Sepharose 4 B in a suitable buffer and the complex is poured into a column and rinsed. An example of a suitable coupling buffer is sodium citrate having a molarity of from about 0.1 to about 2. The coupling buffer is removed, e.g., by rinsing with a neutral isotonic solution, e.g., tris buffer. The latter may also be used to rinse the column.

HB$_s$Ag-positive plasma which has been converted to serum is dialyzed against the same buffer used to remove the coupling buffer, and passed into the column to adsorb HB$_s$Ag by forming an HB$_s$Ab-HB$_s$Ag complex. The column is flushed once to free unadsorbed sample, e.g. with 0.1 M tris buffer, and again to remove nonspecifically bound protein molecules, e.g. with 0.5 M tris buffer. The HB$_s$Ab-HB$_s$Ag complex is then dissociated, e.g. by treatment with NaSCN, and dialyzed to yield purified HB$_s$Ag.

The following examples illustrate the present invention without, however, limiting the same thereto.

EXAMPLE 1

HB$_s$Ag prepared according to Example 1 of U.S. Pat. No. 4,017,360 is adsorbed on alum. Doses, 1.0 ml each, containing 20 µg/ml are injected into guinea pigs at 0, 14 and 56 day intervlas. The animals are bled at the 12th and 16th week following first injection to obtain HB$_s$Ab-positive serum 70 ml of which is dialyzed against 3 M ammonium sulfate overnight at 5° C. to precipitate gamma globulin containing HB$_s$Ab. The precipitated globulin is dissolved in phosphate buffered saline (PBS) to a volume of 15 ml and dialyzed against PBS to remove ammonium sulfate. The dialyzed globulin is then passed through a 5×90 cm Sephadex G-200 column, equilibrated with PBS, to isolate the 7 S globulin fraction. The 7 S globulin fraction is dialyzed overnight against 3.0 l of 0.1 M citrate buffer, pH 6.5. The activated CNBr Sepharose 4 B is prepared with a final rinse in 2.0 l of 0.1 M citrate buffer, pH 6.5. The 7 S globulin fraction and the activated Sepharose 4 B are reacted together at 5° C. for 20 hours with gentle mixing. The Sepharose 4B-HB$_s$Ag complex is collected on a glass filter and rinsed with 1.0 l of 0.1 M Tris saline buffer, pH 7.4. The Sepharose 4B-HB$_s$Ab complex is poured into a 1.6×70 L cm column and rinsed again with 100 ml of 0.1 M Tris buffer, pH 7.4. HB$_s$Ag-positive plasma, 15 ml, which has been converted to serum and dialysed against 0.1 M Tris saline buffer, pH 7.4, is passed into the column to adsorb HB$_s$Ag by formation of a HB$_s$Ab-HB$_s$Ag complex. The complex is washed sequentially with 50 ml of 0.1 M and 50 ml 0.5 M Tris saline buffer, pH 7.4, and eluted with 50 ml 3 M NaSCN, pH 7.4. The HB$_s$Ag containing fractions are pooled and dialysed against 3 l of 0.1 M Tris saline buffer, pH 7.4.

What is claimed is:

1. A method for isolating HB$_s$Ag comprising injecting highly purified HB$_s$Ag antigen into a susceptible animal species to stimulate formation of HB$_s$Ab-positive serum, recovering the serum from the animal, treating the serum to separate a globulin fraction containing HB$_s$Ab, further purifying the HB$_s$Ab in the fraction by chromatographic separation, coupling the purified HB$_s$Ag to a linear polysaccharide in the form of a fixed bed, contacting the HB$_s$Ab in the fixed bed with HB$_s$Ag-positive plasma thereby forming an HB$_s$Ab-HB$_s$Ag immune couplex, and separating HB$_s$Ag from the complex.

2. A method according to claim 1 wherein the HB$_s$Ag-positive plasma is converted to serum before contacting the HB$_s$Ab in the fixed bed.

* * * * *

UNITED STATES PATENT AND TRADEMARK OFFICE
CERTIFICATE OF CORRECTION

PATENT NO. : 4,181,713

DATED : 1/1/80

INVENTOR(S) : McAleer et al.

It is certified that error appears in the above—identified patent and that said Letters Patent is hereby corrected as shown below:

Column 3, line 3, change "HBsAg" to --HBsAb---.

Signed and Sealed this

Fourteenth Day of September 1982

[SEAL]

Attest:

GERALD J. MOSSINGHOFF

Attesting Officer

Commissioner of Patents and Trademarks